US008633165B2

(12) United States Patent
Hutchinson et al.

(10) Patent No.: US 8,633,165 B2
(45) Date of Patent: Jan. 21, 2014

(54) NEUROPROTECTIVE EFFECTS OF 2DG IN TRAUMATIC BRAIN INJURY

(75) Inventors: Elizabeth Brooke Hutchinson, Middleton, WI (US); Mary Elizabeth Meyerand, Cross Plains, WI (US); Paul Anthony Rutecki, Madison, WI (US); Thomas Peter Sutula, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/198,376

(22) Filed: Aug. 4, 2011

(65) Prior Publication Data

US 2012/0065150 A1 Mar. 15, 2012

Related U.S. Application Data

(60) Provisional application No. 61/370,729, filed on Aug. 4, 2010.

(51) Int. Cl.
*A61K 31/7004* (2006.01)
(52) U.S. Cl.
USPC ............................................................ 514/23
(58) Field of Classification Search
USPC ............................................................ 514/23
See application file for complete search history.

(56) References Cited

U.S. PATENT DOCUMENTS

| 7,557,085 | B2 | 7/2009 | Roopra et al. | |
|---|---|---|---|---|
| 7,795,227 | B2 * | 9/2010 | Kriegler et al. | 514/23 |
| 2006/0088517 | A1 * | 4/2006 | Kriegler et al. | 424/94.61 |
| 2006/0287253 | A1 | 12/2006 | Kriegler et al. | |

FOREIGN PATENT DOCUMENTS

WO 2006002121 A2 1/2006

OTHER PUBLICATIONS

Combs et al., "Glycolytic inhibition by 2-deoxyglucose reduces hyperglycemia-associated mortality and morbidity in the ischemic rat," 1986, Stroke 17:989-994.
Database CA Chemical Abstracts Service. Columbus. Ohio. US; Han. IN OK, et al. "Glucosamine for preventing and treating inflammatory brain".XP002662120. retrieved from STN Database accession No. 2010:181258 abstract & KR 2010.
Dixon et al., "A controlled cortical impact model of traumatic brain injury in the rat," 1991, J Neuro. Meth. 39:253-262.
Duan, et al., Dietary Restriction and 2-Deoxyglucose Administratie Improve Behavioral Outcome and Reduce Degeneration of Dopaminergic neurons in models of Parkinson's Disease, 1999, Journal of Neuroscience Research, 57:195-206.
Garriga-Canut et al., "2-Deoxy-D-glucose reduces epilepsy progression by NRSF-CtBP-dependent metabolic regulation of chromatin structure," 2006, Nat Neurosci. 9:1382-1387.

Kaplan et al., "Effects of 2-Deoxyglucose on Drug-sensitive and Drug-resistant Human Breast Cancer Cells: Toxicity and Magnetic Resonance Spectroscopy Studies of Metabolism," Cancer Research,1990, 50:544-551.
Kuhnz and Gieschen, "Predicting the Oral Bioavailability of 19-Nortestosterone Progestins In Vivo from Their Metabolic Stability in Human Liver Microsomal Preparations in Vitro," Drug Metabolism and Disposition, 1998, 26:1120-1127.
Lee, et al., "2-Deoxy-D-Glucose Protects Hippocampal Neurons Against Excitotoxic and Oxidative Injury: Evidence for the involvement of Stress proteins," 1999, Journal of Neuroscience Research, 57:48-61.
Loane et al., "Neuroprotection for traumatic brain injury: translational challenges and emerging 20 therapeutic strategies," 2010, TIPS 31: 596.
Niwa, et al.: "Prevention of ischemia-induced hippocampal neuronal damage by 2-deoxy-D-glucose in gerbils," 1999, Life Sciences, 64:PL193-PL198.
Oravcova et al., "Drug-protein binding studies new trends in analytical and experimental methodology," 1996, J Chromat. B, 677:1-28.
Park, et al., : 2-Deoxy-d-glucose protects neural progenitor cells against oxidative stress through the activation of AMP-activated protein kinase. 2009, Neuroscience Letters, 449: 201-206.
Racine et al., "Modification of seizure activity by electrical stimulation. 2. Motor seizures," 1972, Electroencephalogr. Clin. Neurophysiol. 32: 281-294.
Sowden et al., "Carbohydrate C-Nitroalcohols: the Acetylated Nitroölefins," 1947, JACS 69:1048.
Stafstrom, "Epilepsy: a review of selected clinical syndromes and advances in basic science," 2006, J Cerebral Blood Flow & Metab., 26: 893-1004.
Stafstrom et al., "Anticonvulsant and antiepileptic actions of 2-deoxy-D-glucose in epilepsy models," 2009, Ann Neural. 65: 435-447.
Stein et al., "Targeting tumor metabolism with 2-deoxyglucose in patients with castrate-resistance prostate cancer and advanced malignancies," 2010, Prostate 70: 1388-94.
Sutula, "Mechanisms of progression: current theories and perspectives from neuroplasticity in adulthood and development," 2004, Epilepsy Research 60:161-172.
Sutula & Dudek, "Unmasking recurrent excitation generated by mossy fiber sprouting in the epileptic dentate gyrus: an emergent property of a complex system," 2007, Prog Brain Res 163: 543-566.
Tariq, et al., "Protection by 2-deoxy-D-glucose against beta,beta'-iminodipropionitrile-induced neurobehavioral toxicity in mice," 1999, Exp Neurol. 158:229-33.

(Continued)

*Primary Examiner* — Wu-Cheng Winston Shen
*Assistant Examiner* — Yih-Horng Shiao
(74) *Attorney, Agent, or Firm* — McDonnell Boehnen Hulbert & Berghoff LLP

(57) ABSTRACT

This invention provides methods for reducing the extent and progression of traumatic brain injury and its deleterious sequellae specifically cognitive decline, post-traumatic epilepsy, post-traumatic stress disorder, and other adverse consequences depending on the progression of the initial injury, comprising administering to a TBI victim in need thereof a therapeutically-effective amount of an antiglycolytic compound, particularly 2-deoxyglucose (2-DG) or glycolysis-inhibiting analogs thereof. The invention also provides pharmaceutical compositions of 2-DG or glycolysis-inhibiting analogs thereof for use in the methods of the invention.

7 Claims, 11 Drawing Sheets

(56) References Cited

OTHER PUBLICATIONS

Wei Jinga, et al.,: "Effects of 2-deoxy-d-glucose on focal cerebral ischemia in hyperglycemic rats," 2003, Journal of Cerebral Blood Flow and Metabolism, 23:556-564.

Bolliger, "2-Deoxy-D-arabino-hexose (2-Deoxy-d-glucose)," in Methods in Carbohydrate Chemistry, vol. I, 1962, (Whistler & Wolfram, eds.), New York Academic Press, pp. 186,189.

Fingl et al., 1975, in "The Pharmacological Basis of Therapeutics", Ch.1, p. 1.

Sutula & Ockuly, "Kindling, spontaneous seizures, and the consequences of epilepsy: more than a model," 2005, in Models of Epilepsy (Pitkanen, Schwartzkroin & Moshe, eds.), Elsevier, Amsterdam, pp. 395-406.

The Merck Index, 12th Ed., Monograph 2951, New Jersey: Merck & Co., 1997.

\* cited by examiner a coronal rat brain sections b ex-vivo MRI   in-vivo MRI c ex-vivo DTI   in-vivo DTI

MD

FA a Fronto-parietal CCI b Fronto-parietal CCI
time effect: p=0.0017 c Temporo-parietal CCI d Temporo-parietal CCI
time effect: p=0.381 a Fronto-parietal CCI

NEUROPROTECTIVE EFFECTS OF 2DG IN TRAUMATIC BRAIN INJURY

This application claims priority to U.S. provisional patent application, Ser. No. 61/370,729, filed Aug. 4, 2010, and hereby incorporates by reference the entirety of the provisional application as filed.

This invention was made with government support under W81XWH-09-1-0492 awarded by the ARMY/MRMC. The government has certain rights in the invention.

BACKGROUND OF THE INVENTION

Traumatic Brain Injury (TBI) is a common acquired disorder of the nervous system with a broad spectrum of severity and heterogeneity ranging from lethal penetrating injuries to closed head injury with concussion. It is estimated that approximately 1.4 million people in the US experience TBI every year caused by transportation and vehicular accidents, falls, sports injuries, gunshot wounds, and child abuse. Of these, at least 1 million are treated in emergency rooms, about 50,000 people die annually from TBI, and about 230,000 are hospitalized and survive. An additional source of TBI is related to military action abroad due to the frequency of blast injuries, which are increasingly common but survivable due to improvements in acute emergency care in contemporary combat zones. While survivability has increased, individuals who survive TBI are often left with significant cognitive and communicative disabilities, behavioral disorders such as post-traumatic stress disorder (PTSD), and long-term medical complications such as epilepsy (PTE).

The emergence of PTE and PTSD after TBI is a prototypical example of an acquired brain injury leading to adverse long-term functional consequences. PTE and PTSD may develop and progress despite long intervals after the initial injury, implying that neuronal and brain circuit plasticity initiated by the injury may contribute to development of these disorders. Neural plasticity is the capacity of neurons and neural circuits in the brain to undergo structural and functional modification in response to experience, activity, and injury. While the adult brain was once regarded as "hardwired" with only limited capacity for adaptation, alteration, and reorganization of function, plasticity is now recognized as a fundamental property of the brain that plays a role not only in development but in learning, memory, cognition, pathological processes, and recovery of function after brain injury. Plasticity is defined as the ability of the brain to undergo changes in structure and function. Cellular processes underlying plasticity are now thought to operate at every level of biological organization in the brain, including molecular and cellular levels as well as circuits, networks, and systems. In regard to TBI, plasticity has been implicated as a potential influence on recovery of function after damage, but in addition, processes of plasticity are also hypothesized to contribute to long-term adverse consequences such as PTE, specifically during the latent period from initial injury to emergence of symptomatic seizures. Development of PTE, PTSD or other deleterious sequellae of TBI is unpredictable, even in individuals who experience TBI of apparent comparable severity and location.

Currently, TBI therapy is limited primarily to surgical treatment of the initial injury when possible and supportive general medical care. There have been long-standing and continuing efforts to develop new therapies for TBI survivors, with the goal of reducing the initial extent and progression of TBI, and preventing its long-term complications such as PTSD and PTE. Unfortunately, no efficacious therapies for TBI have been demonstrated in the art. However, a wide variety of agents have been evaluated in experimental models of TBI and in clinical trials in TBI patients, comprising more than 250 clinical trials that are underway for TBI which include studies of both marketed drugs and new chemical entities in preclinical development. Thus, there is a need in the art to develop methods and compounds for treating TBI and its consequences.

SUMMARY OF THE INVENTION

The invention provides methods and pharmaceutical compositions for reducing the incidence, frequency, duration or severity of deleterious sequellae of traumatic brain injury in an animal, particularly structural progression of an initial acute injury, progressive brain tissue loss and structural abnormality, progressive cognitive decline, post-traumatic epilepsy, posttraumatic stress disorder, or other adverse consequences of the initial traumatic brain injury, by administering to the animal a therapeutically-effective amount of an antiglycolytic compound. In particular embodiments, the pharmaceutical composition comprises a therapeutic amount of 2-deoxyglucose or a glycolysis-inhibiting analog thereof. The methods of the invention are advantageously applied to a human having a traumatic brain injury, in non-limiting examples acquired by transportation and vehicular accidents, falls, sports injuries, gunshot wounds, child abuse or military action. According to the methods set forth herein, the antiglycolytic compound, particularly 2-DG and glycolysis-inhibiting analogs thereof, is administered as a pharmaceutical composition after TBI, either acutely, chronically or both. Also provided by the invention are pharmaceutical compositions comprising an antiglycolytic compound, particularly 2-DG or a glycolysis-inhibiting analog thereof, and one or more pharmaceutically-acceptable excipients, wherein the pharmaceutical composition is formulated for parenteral, oral, or nasal administration.

Specific preferred embodiments of the present invention will become evident from the following more detailed description of certain preferred embodiments and the claims.

BRIEF DESCRIPTION OF THE DRAWINGS

An understanding of the invention is facilitated by reference to the drawings.

FIG. 1a shows coronal rat brain sections assessed histologically with cresyl violet staining and an atlas page for reference. FIG. 1b shows illustrative ex vivo and in vivo MRI images of coronal rat brain sections for comparison. FIG. 1c shows ex vivo and in vivo DTI images mapping mean diffusion (MD) and fractional anisotropy (FA).

FIGS. 2a through 2d are in vivo images and DTI maps of rat brains as used in the experiments described, wherein FIG. 2a shows an FA map; FIG. 2b shows an MD map and FIGS. 2c (hippocampus) and 2d (lateral ventricles) depict displacement of region of interest (ROI) masks for a temporo-parietal controlled cortical impact (CCI) injured animal.

FIG. 8a shows FA maps showing hyperintensity (arrow) in the ipsilateral hippocampus of an animal with temporo-parietal CCI that is absent in the fronto-parietal CCI injured animal. FIG. 8b shows the mean laterality index (LRI) of FA values for fronto-parietal and temporo-parietal CCI groups across the three time points investigated (7, 30 and 180 days) and indicates increased laterality in the temporo-parietal CCI, but not fronto-parietal CCI group. The error bars report standard error.

DETAILED DESCRIPTION OF PREFERRED EMBODIMENTS

Figure 1:
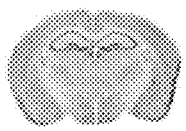
FIGS. 1a through 1c illustrate histological, diffusion tensor imaging (DTI), and magnetic resonance imaging (MRI) sections of rat brain in vivo or ex vivo.
Figure 1:
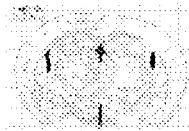
Figure 1:
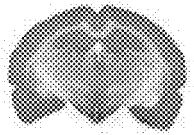
Figure 1:
Figure 1:
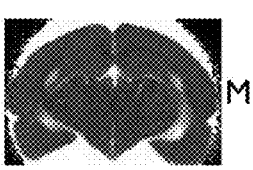
Figure 1:
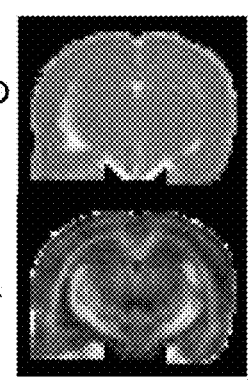
Figure 2:
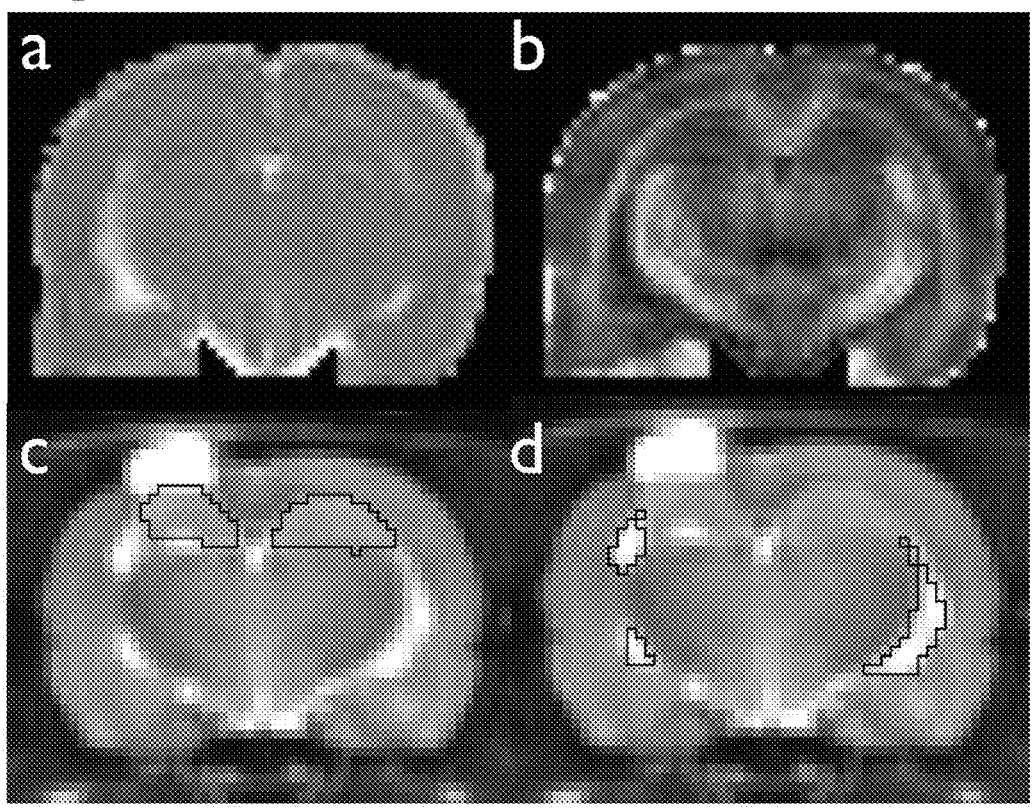

This invention provides methods for reducing the severity and deleterious sequellae of TBI, which include particularly progressive neurological dysfunction, post-traumatic epilepsy (PTE), and post-traumatic stress disorder (PTSD), comprising administering to a TBI victim in need thereof a therapeutically-effective amount of 2-deoxyglucose (2-DG) or glycolysis-inhibiting analogs thereof. The invention also provides pharmaceutical compositions of 2-DG or glycolysis-inhibiting analogs thereof for use in the methods of the invention.

While not wishing to be bound by any hypothesis, this invention depends on the inventors' insight that such deleterious sequellae as PTE may be caused in part by TBI-induced neural plasticity, and that interfering with or altering changes in neural cell metabolism, brain architecture or other changes associated with TBI can prevent or at least reduce the frequency, incidence or severity of such adverse consequences. To address the clinical need for a therapy for TBI and its consequences, the effects of treatment of TBI experimentally-induced in an animal model using the glycolytic inhibitor 2-deoxy-D-glucose was assessed. As disclosed herein, unique strains of rats selectively bred for susceptibility and resistance to kindling, a phenomenon of activity-dependent neural plasticity and a model of limbic epilepsy, were used.

As used herein, the term "antiglycolytic compound" is intended to encompass compounds that modulate glucose metabolism, particularly in brain cells after TBI and that develop or are at risk for development of deleterious sequellae of TBI including in particular PTE, preferably in a human. The term specifically encompasses compounds that inhibit glycolytic enzymes, particularly hexokinase (E.C. 2.7.1.1), glucokinase (E.C. 2.7.1.2), glucose-1-phosphate isomerase (E.C. 5.3.1.9), 6-phosphofructo-1-kinase (E.C. 2.7.1.11), fructose bisphosphate aldolase (E.C. 4.1.2.13), glyceraldehyde-3-phosphate dehydrogenase (E.C. 1.2.1.12), triose phosphate isomerase (E.C. 5.3.1.1), phosphoglycerate kinase (E.C. 2.7.2.3), phosphoglyceromutase (E.C. 5.4.2.1), or pyruvate kinase (E.C. 2.7.1.40). The term also includes compounds that inhibit glucose transporter proteins, particularly glucose transporters known in the art as GLUT1 (SLC2A1, Accession Number AC023331), GLUT2 (SLC2A2, AC068853), GLUT3 (SLC2A3, AC007536), GLUT4 (SLC2A4, AC003688), GLUT5 (SLC2A5, AC041046), GLUT6 (SLC2A6, AC002355), GLUT7 (SLC2A7, AL356306), GLUT8 (SLC2A8, AL445222), GLUT9 (SLC2A9, AC005674), GLUT10 (SLC2A10, AC031055), GLUT11 (SLC2A11, AP000350), GLUT11 (SLC2A11, AP000350), GLUT12 (SLCA12, AL449363), or GLUT13 (SLCA13, AJ315644). In preferred embodiments, an antiglycolytic compound of the invention is 2-deoxyglucose or derivatives thereof that are converted to 2-DG in an animal, or a related deoxy-substitution of glucose, such as 3-deoxy-D-glucose, 4-deoxy-D-glucose, 5-deoxy-D-glucose, combinations of other deoxy-glucose substitutions such as 2, n-deoxy-D-glucose (where n=3-5), compounds designated by permutations of the formula n, m deoxy-D-glucose (where n=2-5 and m=integers from 2-5 excluding n). In additional preferred embodiments, the antiglycolytic compound is a sugar that can be metabolized into 2-DG, such as 2-deoxy-D-galactose, as well as disaccharide embodiments such as lactose and sucrose analogues containing 2-DG, and halogenated and other conjugated derivatives of deoxy sugars (as set forth above), such as fluoro-2-deoxy-D-glucose, conjugated deoxy sugars (as set forth above) that are metabolized to 2-DG, and antiglycolytic compounds having antiglycolytic effects similar to 2-DG. More preferably, an antiglycolytic compound of the invention is 2-deoxy-D-glucose (2-DG) or 3-bromopyruvate, which also inhibits enzymes of the glycolytic pathway.

As used herein, an "effective amount" or "therapeutically effective amount" of an antiglycolytic compound is defined as an amount that when administered to an animal, preferably a human, more preferably a human suffering from TBI, including both adults and juvenile humans, reduces the frequency, incidence, duration or severity of deleterious sequellae of TBI, particularly PTE. "Effective amounts" of said antiglycolytic compounds are those doses that produce subnanomolar to millimolar concentrations of a compound such as 2-deoxyglucose in blood or plasma, and will depend on species, pharmacokinetics, and route of administration. In rats, an "effective dose" of 2-DG is 40 mg/kg by intraperitoneal or subcutaneous administration at 30 minutes before, and then 250 mg/kg immediately after TBI induction and then daily for 2 weeks, but lesser doses may also be effective. Effective doses and administration of 2-DG are advantageously determined in view of established data on safety and tolerance in humans for 2-DG administration in other applications, inter alia treatment of cancer (as disclosed in Stein et al., 2010, "Targeting tumor metabolism with 2-deoxyglucose in patients with castrate-resistance prostate cancer and advanced malignancies," *Prostate* 70: 1388-94, incorporated by reference herein). As provided herein, antiglycolytic compounds, particularly 2-DG and glycolysis-inhibiting analogs thereof, can be administered acutely or chronically after TBI, or prophylactically in instances where an individual is at risk for TBI (including but not limited to soldiers for example in a war zone or other hostile area).

In certain embodiments, the present invention specifically provides antiglycolytic compounds 2-deoxy-D-glucose (2-DG) and pharmaceutical formulations thereof as a treatment that reduces the frequency, incidence, duration or severity of deleterious sequellae of TBI, particularly PTE, as well as alterations in neurological and neuropsychiatric dysfunction. This invention includes antiglycolytic compounds that are 2-DG and related deoxy-substitutions of glucose (as described above), halogenated derivatives and conjugates of these compounds that also block glycolysis, sugars such as 2-deoxy-D-galactose and other compounds that are metabolized into 2-DG and act in the central nervous system by inhibiting glycolysis, and compounds modifying reactions in other metabolic pathways that mimic the effects of glycolytic inhibition on those pathways and have anticonvulsant and antiepileptic effects.

2-DG is known in the art and itself and derivatives thereof have been used medicinally, particularly as a radiolabeled tracer molecule in positron emission tomography (PET) scans of myocardium for diagnosing ischemic heart disease and brain seizures in humans, as well as certain malignancies (see www.fda.gov/cder/regulatory/pet/fdgoncologyfinal.htm, visited Dec. 23, 2003). 2-DG has also been used as a chemotherapeutic agent against breast cancer (Kaplan et al., 1990, *Cancer Research* 50: 544-551).

To address the clinical need for an effective therapy for TBI and to determine whether modification of TBI-related neural plasticity could have favorable therapeutic effects, 2-deoxy-D-glucose, a glucose analogue and glycolytic inhibitor, was administered to animals and structural damage after CCI measured using MRI and DTI. 2DG is a well-known inhibitor of glycolysis that differs from glucose only by removal of a hydroxyl group at the 2 position. 2DG undergoes uptake by glucose transporters and phosphorylation to 2DG-6P, but because this metabolite cannot undergo isomerization by glucose-6P isomerase (GPI) to fructose-6P, subsequent steps of glycolysis and flux through the glycolytic pathway are inhibited. In previous studies, 2DG reduced brain damage initiated by seizures induced by kainic acid (Mattson, 1999, "Dietary restriction and 2-deoxyglucose administration improve behavioral outcome and reduce degeneration of dopaminergic neurons in models of Parkinson's disease," *J. Neurosci. Res.* 57: 195-206) or ischemia (Combs et al., 1986, "Glycolytic inhibition by 2-deoxyglucose reduces hyperglycemia-associated mortality and morbidity in the ischemic rat," *Stroke* 17: 989-994), but effects of 2DG on TBI have not been reported. In more recent in vitro and in vivo screening studies in experimental epilepsy models, 2DG was discovered to have acute anticonvulsant effects (Stafstrom et al., 2009, "Anticonvulsant and antiepileptic actions of 2-deoxy-D-glucose in epilepsy models," *Ann Neurol.* 65: 435-447) and chronic disease-modifying antiepileptic actions against progressive activity-dependent, seizure-induced plasticity evoked by kindling (Garriga-Canut et al., 2006, "2-Deoxy-D-glucose reduces epilepsy progression by NRSF-CtBP-dependent metabolic regulation of chromatin structure," *Nat Neurosci.* 9: 1382-1387). The effects of 2-DG on convulsions and seizures are also disclosed in co-owned U.S. Pat. Nos. 7,795,227 and 7,557,085 and U.S. Patent Applications, Publication No. 2006/0287253 the entirety of said disclosures being incorporated by reference herein.

Anticonvulsant activity of 2DG includes acute in vitro reduction of epileptic discharges evoked in hippocampal brain slices by 7.5 mM $[K^+]_o$, blockade of $K^+$ channels by 4-amino-pyridine, antagonism of $GABA_A$ receptors by bicuculline, and the metabotropic Group I agonist dihydroxyphenylglycine (DHPG), suggesting that the acute anticonvulsant actions of glycolytic inhibition by 2DG are broadly suppressive against a variety of cellular and membrane processes contributing to network synchronization (Stafstrom et al., 2009, Id.). 2DG also has acute in vivo anticonvulsant activity against seizures evoked by 6 Hz and audiogenic stimulation in mice (Stafstrom et al., 2009, Id.), and chronic antiepileptic effects consisting of 2-fold slowing of progression of kindled seizures evoked by perforant path and olfactory bulb stimulation in rats (Garriga-Canut et al., 2006, Id.; Stafstrom et al., 2009, Id.). The latter actions of 2DG against progressive circuit plasticity evoked by kindling involved novel mechanisms of metabolic regulation of activity-dependent increases in BDNF and trkB, which are required for kindling progression and are mediated by the transcriptional repressor Neuron Restrictive Silencing Factor (NRSF), its NADH redox sensor Carboxy-terminal Binding Protein (CtBP), and chromatin modification at the promoter regions of BDNF and trkB (Garriga-Canut et al., 2006, Id.) and in co-owned U.S. Pat. No. 7,557,085, the entirety of said disclosure being incorporated by reference herein.

As provided herein, pharmaceutical compositions comprising 2-DG and methods using said compositions will be understood to encompass preparations of 2-deoxyglucose as the D-stereoisomer, as well as racemic mixtures thereof comprising any combination of D- and L-2-deoxyglucose, provided that the percentage of the D-stereoisomer is greater than zero. 2-DG is available commercially, and preferably is produced according to the standards and guidelines of the pharmaceutical industry and in compliance with all relevant regulatory requirements. 2-DG can also be synthesized using methods well-established in the art (see, for example, THE MERCK INDEX, 12*th* Ed., Monograph 2951, New Jersey: Merck & Co., 1997; Bergmann et al., 1922, *Ber.* 55: 158; Snowden et al., 1947, *JACS* 69: 1048; Bolliger et al., 1954, *Helv. Chim.*

*Acta* 34: 989; Bolliger, 1962, "2-Deoxy-D-arabino-hexose (2-Deoxy-d-glucose)," in METHODS IN CARBOHYDRATE CHEMISTRY, vol. I, (Whistler & Wolfram, eds.), New York Academic Press, pp. 186, 189).

The invention also provides embodiments of said antiglycolytic compounds, particularly 2-DG and glycolysis-inhibiting analogs thereof, as pharmaceutical compositions. The pharmaceutical compositions of the present invention can be manufactured in a manner that is itself known, e.g., by means of a conventional mixing, dissolving, granulating, dragee-making, levigating, emulsifying, encapsulating, entrapping or lyophilizing processes.

Pharmaceutical compositions of the antiglycolytic compounds of the present invention, particularly 2-DG and glycolysis-inhibiting analogs thereof, can be formulated and administered through a variety of means, including systemic, localized, or topical administration. Techniques for formulation and administration can be found in "Remington's Pharmaceutical Sciences," Mack Publishing Co., Easton, Pa. The mode of administration can be selected to maximize delivery to a desired target site in the body. Suitable routes of administration can, for example, include oral, rectal, transmucosal, transcutaneous, or intestinal administration; parenteral delivery, including intramuscular, subcutaneous, intramedullary injections, as well as intrathecal, direct intraventricular, intravenous, intraperitoneal, intranasal, or other appropriate injection routes and sites.

Alternatively, one can administer the antiglycolytic compounds, particularly 2-DG and glycolysis-inhibiting analogs thereof, in a local rather than systemic manner, for example, via injection of the compound directly into a specific tissue, often in a depot or sustained release formulation. Specifically, antiglycolytic compounds and formulations of the invention can be administered locally by devices and local infusion systems to achieve local effects in tissues.

Pharmaceutical compositions for use in accordance with the methods of the present invention thus can be formulated in conventional manner using one or more physiologically acceptable carriers comprising excipients and auxiliaries that facilitate processing of antiglycolytic compounds, particularly 2-DG and glycolysis-inhibiting analogs thereof, into preparations that can be used pharmaceutically. Proper formulation is dependent upon the route of administration chosen.

Such antiglycolytic compounds, particularly 2-DG and glycolysis-inhibiting analogs thereof, can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the antiglycolytic compounds, particularly 2-DG and glycolysis-inhibiting analogs thereof, can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions. Alternatively, the active ingredient can be in powder form for constitution with a suitable vehicle, e.g., sterile pyrogen-free water, before use. Compounds, particularly 2-DG and glycolysis-inhibiting analogs thereof, can also be formulated in rectal compositions such as suppositories or retention enemas, e.g., containing conventional suppository bases such as cocoa butter or other glycerides.

For injection, antiglycolytic compounds, particularly 2-DG and glycolysis-inhibiting analogs thereof, can be formulated in appropriate aqueous solutions, such as physiologically compatible buffers such as Hank's solution, Ringer's solution, lactated Ringer's solution, or physiological saline buffer. For transmucosal and transcutaneous administration, penetrants appropriate to the barrier to be permeated are used in the formulation. Such penetrants are generally known in the art.

For oral administration, antiglycolytic compounds, particularly 2-DG and glycolysis-inhibiting analogs thereof, can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose and starch preparations such as, for example, maize starch, wheat starch, rice starch, potato starch, gelatin, gum tragacanth, microcrystalline cellulose, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients, particularly 2-DG and glycolysis-inhibiting analogs thereof, in admixture with filler such as lactose, binders such as starches, and/or lubricants such as talc or magnesium stearate and, optionally, stabilizers. In soft capsules, antiglycolytic compounds can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the compositions can take the form of tablets or lozenges formulated in conventional manner.

For administration by inhalation antiglycolytic compounds, particularly 2-DG and glycolysis-inhibiting analogs thereof, for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

In addition to the formulations described previously antiglycolytic compounds, particularly 2-DG and glycolysis-inhibiting analogs thereof, can also be formulated as a depot preparation. Such long acting formulations can be administered by implantation (for example subcutaneously or intramuscularly) or by intramuscular injection. Thus, for example, the antiglycolytic compounds can be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for hydrophobic embodiments of the antiglycolytic compounds of the invention, particularly 2-DG and glycolysis-inhibiting analogs thereof, is a co-solvent system comprising benzyl alcohol, a nonpolar surfactant, a water-miscible organic polymer, and an aqueous phase. The co-solvent system can be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of polysorbate 80; the fraction size of polyethylene glycol can be varied; other biocompatible polymers can replace polyethylene glycol, e.g. polyvinyl pyrrolidone; and other sugars or polysaccharides can substitute for dextrose.

Alternatively, other delivery systems can be employed. Liposomes and emulsions are well known examples of delivery vehicles or carriers for hydrophobic drugs. Certain organic solvents such as dimethylsulfoxide also can be employed, although usually at the cost of greater toxicity. Additionally, antiglycolytic compounds, particularly 2-DG and glycolysis-inhibiting analogs thereof, can be delivered using a sustained-release system, such as semipermeable matrices of solid hydrophobic polymers containing the therapeutic agent. Various sustained-release materials have been established and are well known by those skilled in the art. Sustained-release capsules can, depending on their chemical nature, release the antiglycolytic compounds for a few weeks up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients, particularly 2-DG and glycolysis-inhibiting analogs thereof, are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

The invention also provides formulations of the antiglycolytic compounds, particularly 2-DG and glycolysis-inhibiting analogs thereof, as foodstuffs, food supplements or as a component of a food for an animal, preferably a human, more preferably a human suffering from TBI and at risk for or experiencing the deleterious sequellae thereof, particularly PTE, most preferably adult or juvenile humans with TBI.

For any antiglycolytic compounds used in the method of the invention, the therapeutically effective dose can be estimated initially from in vitro assays, as disclosed herein, or using art-recognized animal model systems or a combination thereof. For example, a dose can be formulated in animal models to achieve a circulating concentration range that includes the $EC_{50}$ (effective dose for 50% increase) as determined in vitro, i.e., the concentration of the compound, particularly 2-DG and glycolysis-inhibiting analogs thereof, which achieves a reduction in DTI or MRI measures of structural brain damage in 50% of animals with TBI. Such information can be used to more accurately determine useful doses in humans.

It will be understood, however, that the specific dose level for any particular patient will depend upon a variety of factors including the activity of the antiglycolytic compounds employed, body weight, general health, gender, diet, time of administration, route of administration, and rate of excretion, drug combination, the severity and extent of the TBI and adverse consequence thereof, particularly PTE, in the patient undergoing therapy and the judgment of the prescribing physician and in particular the age of the patient, who is may be an adult, a juvenile, a child or an infant.

Preferred antiglycolytic compounds, particularly 2-DG and glycolysis-inhibiting analogs thereof, provided by the invention will have certain pharmacological properties. Such properties include, but are not limited to oral bioavailability, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcová et al. (1996, *J. Chromat. B* 677: 1-27). In vitro half-lives of antiglycolytic compounds may be predicted from assays of microsomal half-life as described by Kuhnz and Gieschen (1998, *Drug Metabolism and Disposition,* 26: 1120-1127).

Toxicity and therapeutic efficacy of said antiglycolytic compounds, particularly 2-DG and glycolysis-inhibiting analogs thereof, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio between $LD_{50}$ and $ED_{50}$. Antiglycolytic compounds, particularly 2-DG and glycolysis-inhibiting analogs thereof, that exhibit high therapeutic indices are preferred. The data obtained from these cell culture assays and animal studies can be used in formulating a range of dosage for use in humans. The dosage of such antiglycolytic compounds, particularly 2-DG and glycolysis-inhibiting analogs thereof, lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

For example, dosage amount and interval of 2-DG administration can be adjusted individually to reduce incidence, frequency, duration or intensity of deleterious sequellae of TBI, particularly PTE, using doses of 40 mg/kg or less to higher as tolerated to reduce seizure frequency and minimize toxicity. Doses of 250 mg/kg were well tolerated in rats. A practitioner skilled in the art can adjust dosage in the range of 2-250 mg/kg and the timing of administration to produce prolonged neuroprotectant effects. Efficacious dosage amounts can be adjusted in children and adults, for establishing effective dosage levels.

For the alternative embodiments such as antiglycolytic compounds, particularly 2-DG and glycolysis-inhibiting analogs thereof, that reversibly inhibit glycolysis, dosage amount and timing of administration of said compounds can be adjusted individually to provide plasma levels of the antiglycolytic compounds that are sufficient to reduce incidence, frequency, duration or intensity of deleterious sequellae of TBI, particularly PTE.

The pharmaceutical compositions disclosed herein can be administered acutely or chronically, and before the advent or development of deleterious sequellae of TBI, particularly PTE, and the route of administration and administered dose chosen accordingly.

The Examples that follow are illustrative of specific embodiments of the invention, and various uses thereof. They are set forth for explanatory purposes only, and are not to be taken as limiting the invention.

EXAMPLE 1

Effects of 2-DG on TBI in Kindling-Susceptible and Kindling-Resistant Rat Strains In the course of developing the invention, particular strains of rats were employed that were resistant or sensitive to the induction of kindled seizures in the brain; while availability of these rats is not necessary to practice the invention as disclosed herein, their use was advantageous in performing the experiments used to demonstrate and developing the invention as disclosed herein. Kindling refers to the progressive, permanent increase in susceptibility to evoked and spontaneous seizures induced by repeated episodes of network synchronization. Kindling is initiated by repeated periodic application of a brief stimulus that evokes repetitive epileptic spikes (an afterdischarge, or AD) accompanied by a brief behavioral seizure. With repeated stimulations, the duration of the evoked ADs and behavioral seizures gradually increases, the strength of the stimulus required to evoke network synchronization decreases, and there is an overall permanent increase in susceptibility to additional seizures culminating eventually in emergence of spontaneous seizures. The acquisition of permanent susceptibility to seizures induced by kindling is accompanied by a predictable sequence of molecular and cellular alterations including neuronal loss, gliosis, and axon sprouting that progressively reorganize neural circuits (Sutula & Dudek, 2007, "Unmasking recurrent excitation generated by mossy fiber sprouting in the epileptic dentate gyms: an emergent property of a complex system," *Prog Brain Res* 163: 543-566; Stafstrom, 2006, "Epilepsy: a review of selected clinical syndromes and advances in basic science," *J. Cerebral Blood Flow & Metab.* 26: 893-1004; Sutula & Ockuly, 2005, Kindling, spontaneous seizures, and the consequences of epilepsy: more than a model, in *Models of Epilepsy* (Pitkanen, Schwartzkroin & Moshe, eds.), Elsevier, Amsterdam, pp. 395-406; Sutula, 2004, "Mechanisms of progression: current theories and perspectives from neuroplasticity in adulthood and development," *Epilepsy Research* 60:161-172). TBI was induced in these rats to determine the effects of TBI and whether 2-DG could affect the incidence, frequency, duration or severity of deleterious sequellae of TBI such as PTE.

Behavioral seizures accompanying evoked ADs can be reliably classified ranging from the least severe (Class I, brief arrest of motion) to the most severe (Class V, secondary generalized tonic-clonic seizures) according to a standardized scale (modified from Racine et al., 1972, "Modification of seizure activity by electrical stimulation. 2. Motor seizures," *Electroencephalogr. Clin. Neurophysiol.* 32: 281-294). The number of evoked ADs required to evoke the first Class V seizure varies as function of the location of the stimulation pathway, and is a reliable measure of the rate of kindling progression. In certain advantageous and informative experiments, TBI was induced in rat strains selectively bred for susceptibility and resistance to kindling evoked by repeated stimulation of the perforant path, the major converging afferent input from the entorhinal cortex into the dentate gyms and hippocampus. In normal outbred Sprague-Dawley rats, ~14-15 stimulations that evoke an AD are required to elicit the first Class V seizure. Rats were selected for susceptibility or resistance to kindled seizures by breeding outbred rats with "slow" kindling rates (>20 ADs to the first Class V seizure), or "fast" kindling rates (<10 ADs to the first Class V seizure). "Slow" males were mated with "slow" females, and "fast" males with "fast" females. Offspring demonstrating "fast" or "slow" kindling rates based on the above criteria were bred in successive generations with other "slow" or "fast" kindling rats to select for the phenotype of kindling susceptibility ("fast" strain) or resistance ("slow" strain). In successive generations these strains were distinguishable based on the number of ADs required to evoke a Class V seizure, and presumably by underlying genetic background influencing the complex molecular and cellular processes predisposing to susceptibility or resistance to neural circuit reorganization.

"Fast" rats and "slow" rats from the $9^{th}$-$11^{th}$ generations selected by these procedures were subjected to TBI induced by the method of controlled cortical impact (CCI) using published protocols (see Dixon et al., 1991, *J. Neuro. Meth.* 39: 253-262). During the induction of TBI by CCI, the rats were deeply anesthetized with isoflurane (3% for induction, 1.5-2.5% for maintenance) and were placed in a stereotaxic frame. After craniotomy with the dura intact, anesthesia was reduced to 1% isoflurane for a 5-min equilibration period and CCI was performed over temporo-parietal cortex (−1 to −6 mm from bregma, below lateral skull ridge) and fronto-parietal cortex (+5.3 to −0.3 mm from bregma, below lateral skull ridge), which are more and less likely, respectively, to damage the hippocampus and amygdala. Brain lesions were induced by a digitally-controlled contusion device using a pneumatically driven impactor with a sterilized rounded stainless steel tip (3-4 mm in diameter) which compresses the cortex with a specified velocity, depth, and dwell time varied to induce a range of injury severity (ranging from mild, with parameters of 4.0 m/s, 1.0 mm deformation, dwell time 50 mS, to severe, at 6.0 m/s, 2.5 mm deformation, dwell time 50 mS). Anesthesia was then administered at maintenance levels (1.5-2.5%), the craniotomy and wound were closed, and the rats were allowed to recover. The location, severity, and progression of induced cortical and subcortical damage was examined by serial in vivo magnetic resonance imaging (MRI) and diffusion tensor imaging (DTI) techniques at 1 week, 1 month, and 6 months after TBI.

The effects of 2DG on TBI induced by CCI in fronto-parietal and temporo-parietal cortex were evaluated in "fast" kindling-susceptible and "slow" kindling-resistant rats. Half of the rats from these strains received 2DG at 40 mg/kg IP 30 min prior to CCI, and then 250 mg/kg immediately after and twice daily for 2 weeks. These rats were compared to control groups with TBI induced by CCI that were treated only with an equivalent volume of saline. Both treatment groups were also compared to sham-injured rats that underwent all aspects of the experimental manipulations except for CCI.

The effects of 2DG treatment on the location, severity, and progression of induced cortical and subcortical damage were assessed in serial in vivo magnetic resonance imaging (MRI) and diffusion tensor imaging (DTI) studies at 1 week, 1 month, and 6 months after TBI as well as high-resolution ex vivo DTI of brains harvested from the same rats following the final in vivo imaging session. DTI is an advanced MRI modality that offers a unique view of the brain in its ability to report quantitative microstructural information at the whole-brain and in vivo scales. The most commonly reported DTI indices are fractional anisotropy (FA), which characterizes the "directionalness" of tissue structure (e.g. high in white matter and low in grey matter and CSF) and mean diffusion (MD), which characterizes water status ("free" or "restricted") due to cellular barriers (e.g. high in CSF and low in tissue). Both indices are known to be sensitive to damage and other structural changes such as tissue/circuit reorganization. This makes DTI an attractive modality to investigate disorders with known or hypothesized structural abnormalities such as TBI.

On the day of scanning the rats were anesthetized with inhaled isoflurane mixed with oxygen (3.5% induction and 1.5-3.0% maintenance during scanning) The rat head was stabilized using a custom built head holder with three point restraint. Animals were maintained at 37.0+/−1.0 degrees C. by a circulating water bath and physiological monitoring of temperature and respiration was performed throughout the scan.

MRI scanning was performed using a Varian 4.7 T scanner and a quadrature birdcage volume coil was used to transmit and receive the MRI signal. Coronal slices were prescribed for anatomical and DTI imaging in a consistent manner for all animals using a sagittal anatomical image and by identifying anatomical landmarks for the placement of slice edges. T2-weighted coronal images were acquired using a multi-slice fast spin echo pulse sequence with the following parameters: TE/TR=65/3500 ms, echo train length=8, FOV=35 mm×35 mm, matrix size=128×128, 11 contiguous slices, slice thickness=1 mm, number of averages=8. Region of interest (ROI) masks used to calculate lateral ventricle volume were generated by thresholding of the T2 weighted image and manual masking to include only the lateral ventricles. Lesion volume was calculated by subtraction of an ipsilateral hemispheric mask excluding lesioned tissue from an ipsilateral mask altered to match the shape of the unaffected contralateral side. Thirty non-collinear diffusion weighted image volumes and 3 unweighted reference image volumes were acquired using a 4-shot echo planar imaging (EPI) sequence with identical spatial parameters (FOV, matrix and slices) to the anatomical images. Image acquisition was respiration-gated with TE/TR=39 ms/>1 s and 6 averages.

To investigate changes identified in vivo, brains were harvested from the rats after imaging at 6 months and ex vivo DTI was performed. For each 7 hour and 2 minute DTI acquisition, 3 brains were simultaneously imaged using a small diameter (3.5 cm) quadrature volume RF coil. A series of multi-slice spin echo images were acquired with TE/TR=24/2000 ms, nex=2 and included 3 non-weighted and 30 diffusion weighted images with a b-value of approximately 1200 s/mm$^2$ and used non-colinear weighting directions. Spatial imaging parameters were FOV=30×30 mm$^2$, matrix=192×192 reconstructed to 256×256, slice thickness=0.5 mm and number of slices=35.

Image processing was performed using FSL tools and custom Matlab (version 7.8.R2009a) code and included: eddy current correction, non-linear tensor fitting and generation of FA and MD maps for analysis. Region of interest (ROI) masks for the hippocampus, frontal lobe, anterior corpus callosum (CC) and posterior CC were created manually by blinded researchers familiar with rat neuroanatomy and based on anatomical landmarks. For the hippocampus and frontal lobes, whole structure values were determined as well as values ipsilateral and contralateral to the side of lesion. In order to quantify the extent to which DTI measures were increased on the ipsilateral vs. contralateral side, a lateralization index was calculated as follows:

$$LRI=(DTI_I-DTI_C)/\tfrac{1}{2}(DTI_I+DTI_C)$$

where $DTI_I$ and $DTI_C$ are the ipsilateral and contralateral DTI values (FA or MD) respectively.

Statistical Analysis.

In order to test the in vivo data for the effects and interactions of the factors included in this study (TBI location, strain, treatment and time interval) on the response variable (imaging measurement of volume or DTI measures) a linear mixed effects (LME) model was employed using the R statistical software package. The advantages of using the LME statistical approach for our longitudinal and multivariate data set is flexibility of modeling individual change across time to test within- and between-group outcomes. The LME model also incorporates effects of missing data points in making statistical inferences and treats time as continuous so that unequally-spaced time points were accounted for. Analysis of variance (ANOVA) was applied to test the model for significant effects and interactions. The statistical output for each response variable was an ANOVA table and those effects and interactions with a p-value of less than 0.1 were further investigated for graphical trends by interaction plots or bar graphs. In cases of factor by time interval interactions, paired T-tests were used to determine the significance of change in response over time. In cases of factor interactions, a second LME model was fit to subsets of the data taken based on one of the interacting factors.

In cases of proportional change, there were not enough time points to use LME modeling, so Student's T tests were used to determine the significance of differences between groups.

Ex vivo data was subjected to ANOVA testing and in cases of interactions unpaired t tests were performed.

Results

A total of 35 rats were used with 4 rats in each of 8 experimental groups and 3 sham-lesioned rats, which served as controls. Volumetric and DTI findings supporting a neuroprotective role for 2DG following TBI included: reduced progressive increase in the volume of the lateral ventricles, reduced progressive increase in ipsilateral MD in the hippocampus, reduced laterality effect for FA in the hippocampus and increase over time toward control values of FA in the anterior corpus callosum. These outcomes are defined and discussed as follows.

Lateral Ventricle Volumes

Figure 3:
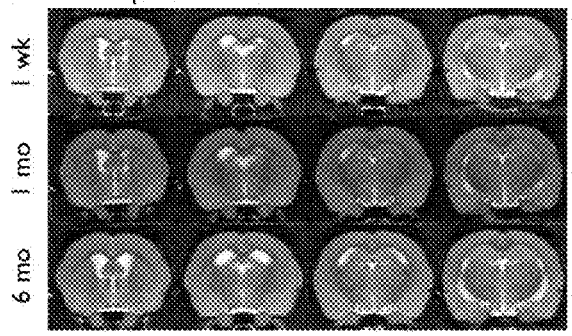
FIG. 3a shows in vivo T2W MRI images for fronto-parietal CCI injured animals used to quantify lateral ventricle volume for this group as shown in FIG. 3b over three time points (1 week, 1 month and 6 months).
FIG. 3c shows T2W MRI DTI images for temporo-parietal CCI injured animals with lateral ventricle volume quantified in FIG. 3d over three time points (1 week, 1 month and 6 months)
Figure 3:
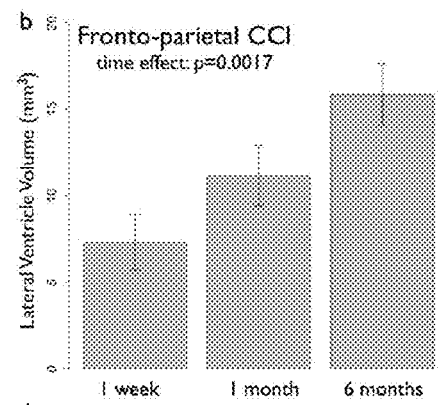
Figure 3:
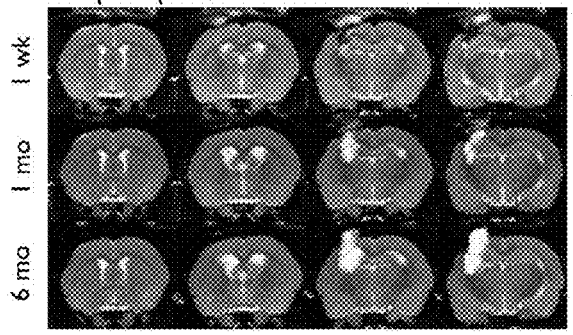
Figure 3:
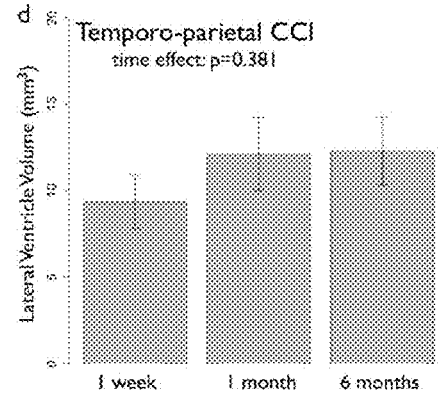
Figure 4:
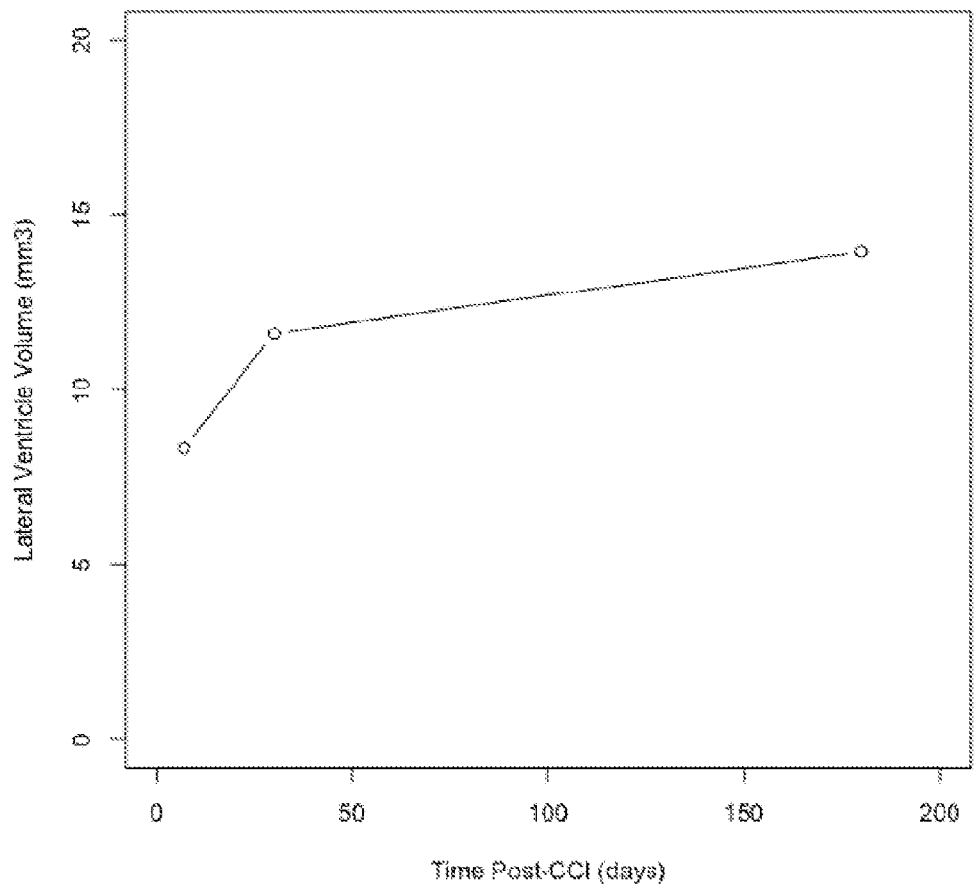
FIG. 4 is a graph showing increasing lateral ventricle volume calculated from in vivo T2W MRI at one week, one month and 6 months post CCI in rats with experimentally-induced fronto-parietal and temporo-parietal TBI.

Lateral ventricle volumes increased over time in individual animals with both fronto-parietal and temporo-parietal CCI as shown in FIG. 3. LME analysis of the experimental groups found a main effect for time interval (p=0.0045) that is characterized by increasing volume over time (see FIG. 4). Enlarged ventricles are a gross measure of brain atrophy and damage, and an increase in ventricle volume over time is indicative of progressive processes suggesting that this TBI model incurs progressive brain atrophy.

Figure 5:
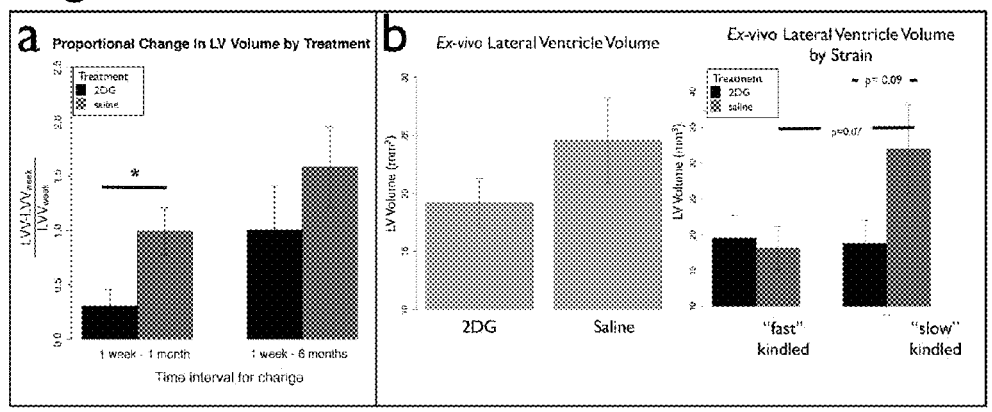
FIG. 5a is a bar graph of mean values for changes in lateral ventricle volumes measured in vivo and expressed as a proportion of lateral ventricle volumes in in vivo T2W MRI images at one week post CCI for saline and 2-DG treated groups of rats with experimentally-induced TBI in both fronto-parietal and temporo-parietal locations. Error bars report the standard error of the mean, and the asterisk indicates that the statistical significance of the changes between one week and one month as determined by paired t-test was $p<0.05$ for the saline but not the 2-DG treated group.
FIG. 5b is a bar graph of mean values for ex vivo lateral ventricle volumes expressed in cubic millimeters comparing the effect of 2DG to saline in all animals and comparing "fast" and "slow" kindling rat strains.

The proportional change in ventricle volume from 1 week to 1 month following injury was significantly greater (p=0.015) for the group treated with saline than the group treated with 2DG (see FIG. 5a). This suggests that 2DG reduced progressive volumetric changes following CCI injury.

Ex vivo lateral ventricle volumes were compared between experimental groups using ANOVA, which found a trend for treatment main effect (p=0.16) and a strain by treatment interaction (p=0.06). These are characterized by the bar graphs in FIG. 5b and indicate greater lateral ventricle volumes for the saline treated group that are most evident for the slow-kindled strain. The interpretation of this finding is consistent with the in vivo results and suggest protection from gross tissue loss by 2DG.

Hippocampal DTI Measures

Figure 6:
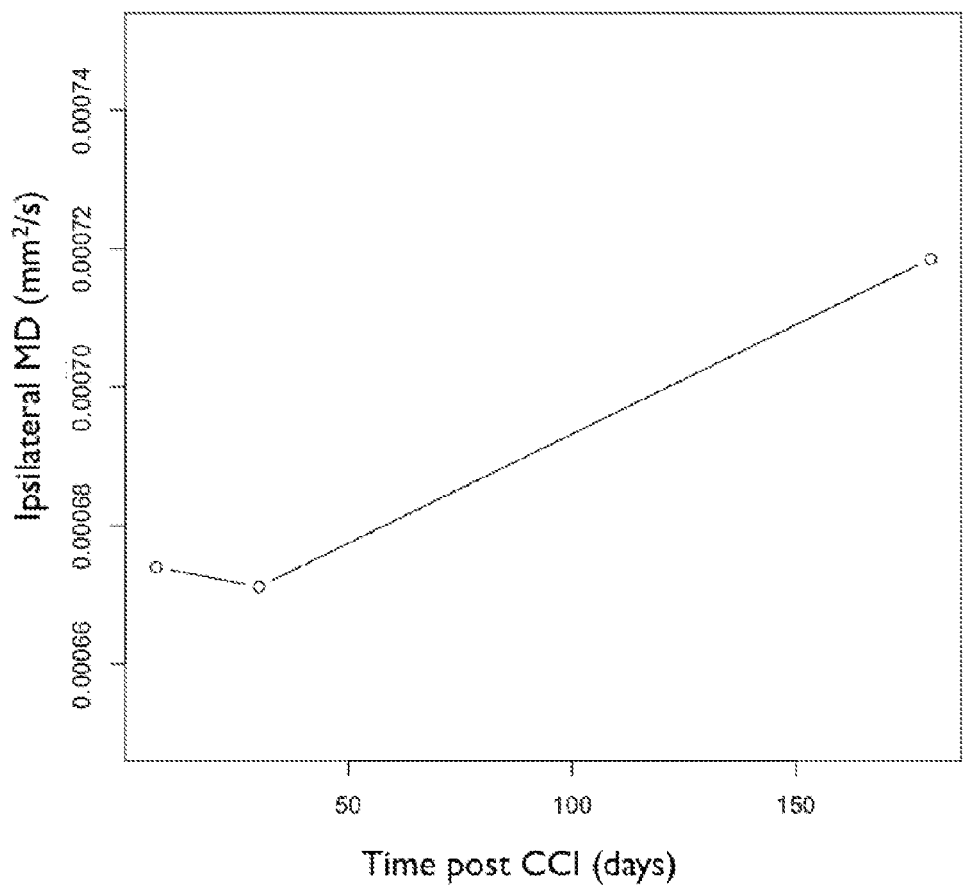
FIG. 6 is a graph showing increased in vivo ipsilateral hippocampal MD at one week, one month and 6 months post CCI in rats having experimentally-induced hippocampal TBI in fronto-parietal and temporo-parietal locations.

Ipsilateral in vivo MD in the hippocampus was found to increase over time in the experimental groups by a main effect for time interval (p=0.0004, see FIG. 6). There was also a trend towards significance for a treatment by time interval interaction (p=0.064) characterized by greater increases in MD by 6 months for saline than 2DG treated groups (see FIG. 7a). A paired t-test found that a difference in MD between 1 week and 6 months was significant for the saline treated groups (p=0.0026), but not for the 2DG treated groups (p=0.289). Since increases in MD are sensitive to a variety of damage mechanisms including edema and atrophy, these results suggested that the saline treated group underwent some progressive damage and the 2DG treated group did not.

Figure 7:
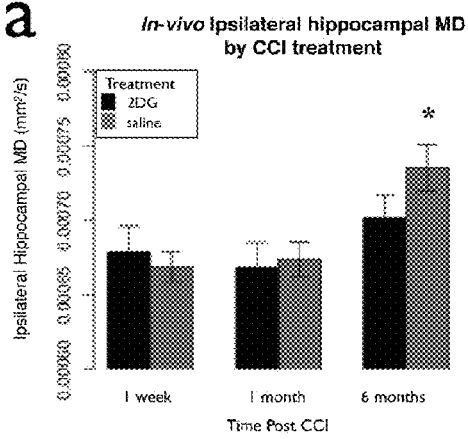
FIG. 7a is a bar graph of mean values for in vivo ipsilateral hippocampal MD at 7, 30 and 180 days post CCI in saline and 2DG treated groups. Error bars report the standard error of the mean, and the asterisk indicates that the statistical significance was $p<0.05$ as assessed by paired t-test statistics for the changes between one week and six months for saline-treated groups, while no significant change was found for 2-DG treated animals or sham-treated controls
FIG. 7b is a bar graph comparing ex vivo ipsilateral hippocampal MD in TBI-induced rats in the presence and absence of 2DG showing reduced values for MD in saline-treated animals compared to 2-DG treated animals and sham-injured controls.
Figure 7:
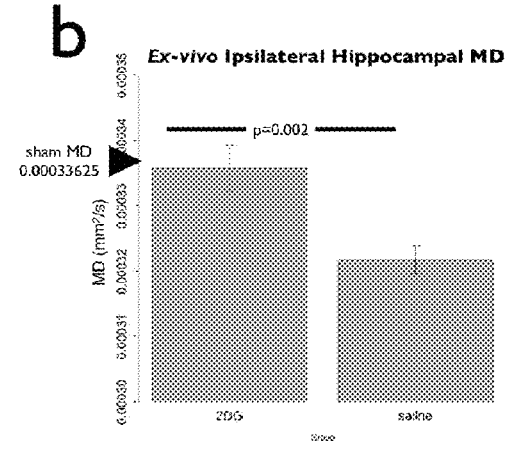

ANOVA of ex vivo ipsilateral hippocampal MD showed a significant main effect for treatment group (p=0.002) between saline and 2DG treated groups where MD values for 2-DG treated animals overlapped with sham injured controls, while saline treated animals showed a decreased in MD. 2-DG treatment thus restored MD measurements to the range of normal values observed in controls, while saline-treated animals showed MD abnormalities (FIG. 7b).

Figure 8:
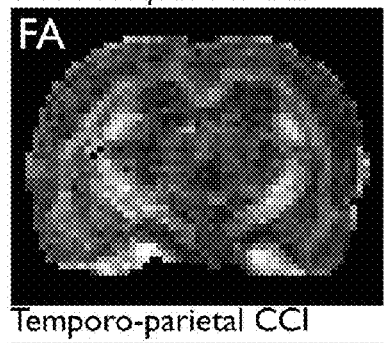
FIGS. 8a and 8b illustrate laterality effects in in vivo hippocampal FA post CCI.
Figure 8:
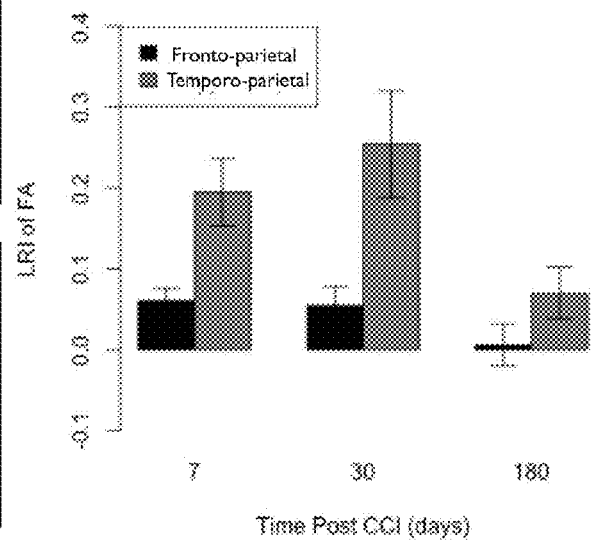

LRI in vivo of FA was found to be increased in temporo-parietal, but not fronto-parietal CCI injured animals by a main effect of TBI location (p=0.0003), which suggested that this measure was sensitive to tissue structure change characterized by increased FA ipsilateral to the side of injury (FIG. 8). These results can be confirmed by histological studies to fully determine the cellular mechanisms of injury that underlie this marker. However, in advance of such studies the leading interpretations are injury dependent plasticity, selective cell loss and tissue structure reorientation due to injury.

Figure 9:
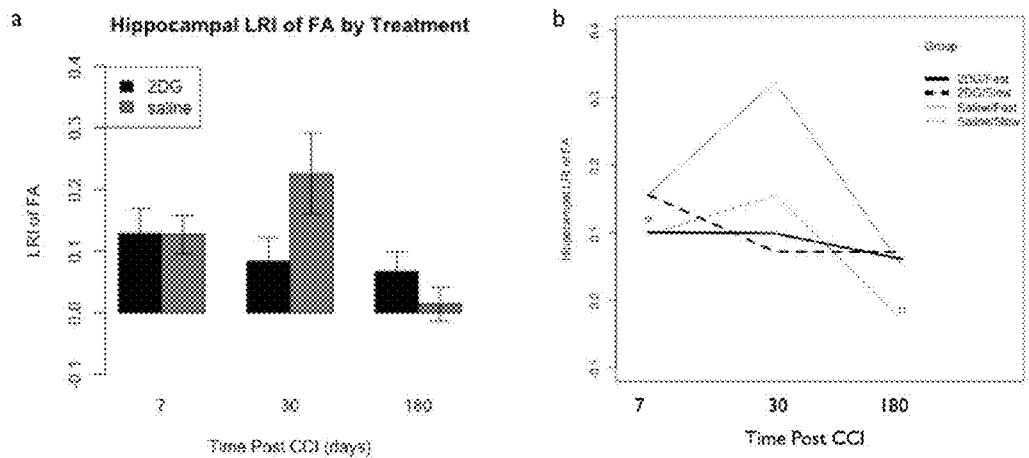
FIG. 9a is a bar graph showing effects of 2DG treatment on in vivo hippocampal FA LRI at 1 week, 1 month, and 6 months where error bars report standard errors.
FIG. 9b shows the effects of 2-DG treatment on hippocampal FA LRI in "fast" and "slow" kindled animals in the presence and absence of 2DG, and demonstrates that 2-DG reduces FA LRI in both strains.

A trend towards significance for an interaction of strain and treatment was found for LRI of in vivo FA as well (p=0.088). This trend was characterized by greater LRI for fast kindled and saline treated groups (FIG. 9), wherein 2DG treatment appeared to abolish the pattern of increased LRI over 1 week to 1 month in both strains. A T-test of saline vs. 2DG treated groups at 1 month found a non-significant trend (p=0.08) towards increased LRI in saline compared to 2DG treated animals. Taken together, these results suggested a role for 2DG in preventing lateralized change in hippocampal FA that follows TBI injury.

Corpus Callosum DTI

In vivo FA values in the corpus callosum (CC) were found to be decreased depending on TBI location with a significant decrease in anterior CC FA for fronto-parietal CCI groups (LME main effect for TBI location, p=0.0297) and a decrease in posterior CC values for temporo-parietal CCI (LME main effect for TBI location, p=0.0067). Reduced FA is most commonly used to determine white matter damage such as axonal degradation and demyelination suggesting that the anterior and posterior CC are damaged according to TBI location.

Figure 10:
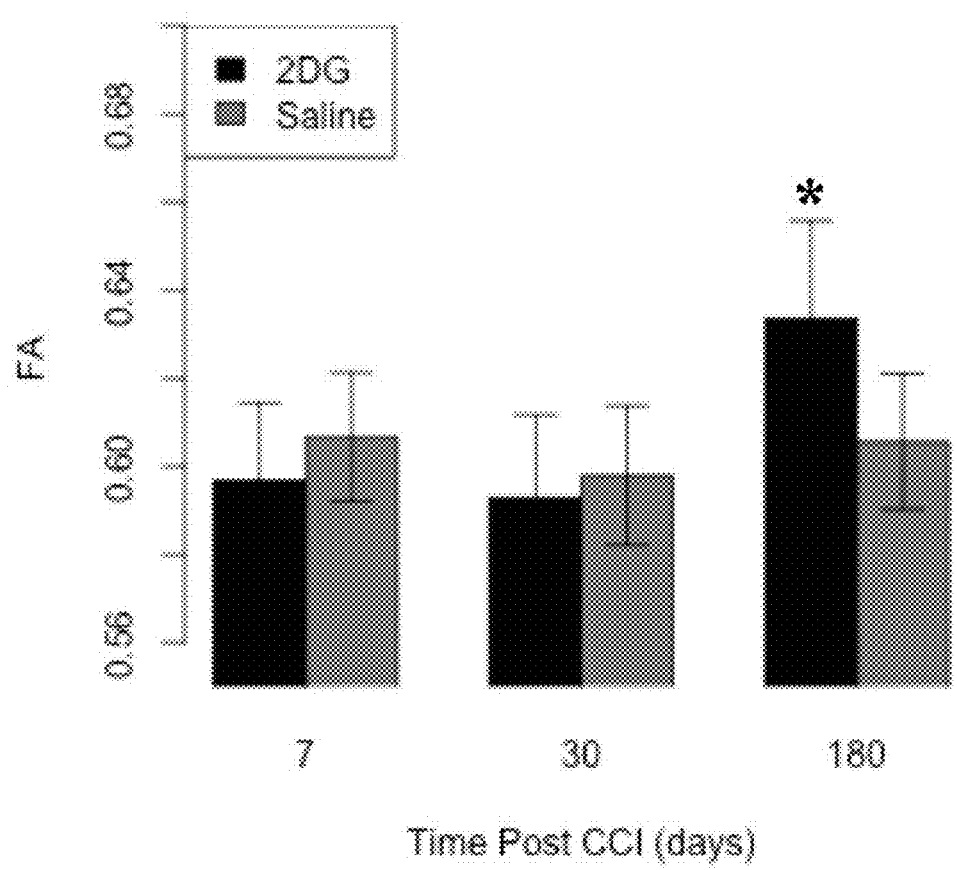
FIG. 10 shows FA in the anterior corpus callosum (aCC) in groups of rats with TBI induced by CCI in fronto-parietal and temporo-parietal locations. 2DG treated groups show an increase in aCC FA by 6 months post-CCI that nearly reaches control values. Error bars report standard error and the asterisk indicates statistical significance of $p<0.05$ for a paired t-test between CC FA at 1 week and 6 months.

As shown in FIG. 10, a trend towards significance for an interaction of treatment by time interval was found for in vivo aCC FA (p=0.073) and when investigated further using paired T-tests, there was a significant change from one week to six months for the 2DG treated groups (p=0.0099), but not the saline treated groups (p=0.8396). This selective increase in FA implies that white matter repair occurs in 2DG treated animals, but not saline treated animals by 6 months post-CCI.

Figure 11:
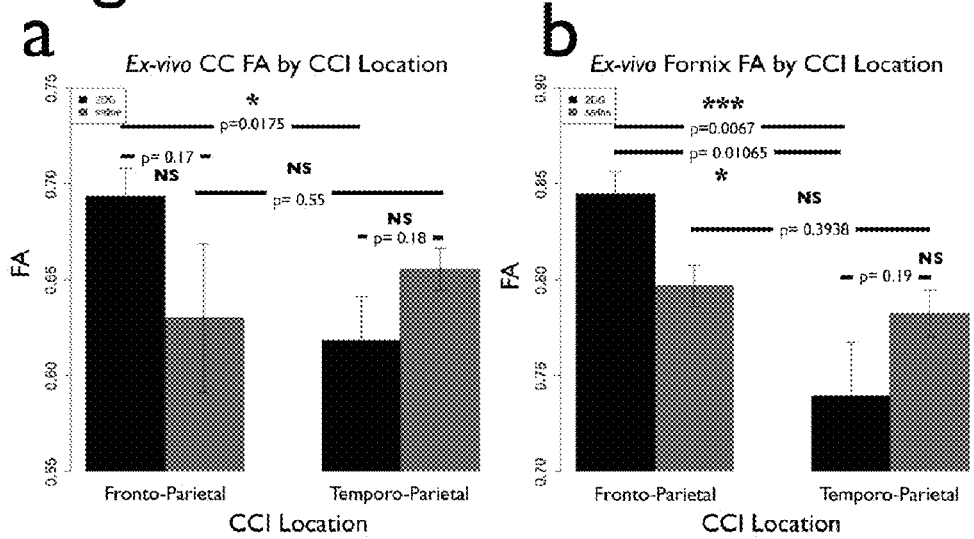
FIG. 11a shows ex vivo FA in the corpus callosum (CC) and fornix in groups of rats with TBI induced by CCI in fronto-parietal and temporo-parietal locations. CC FA (results shown in FIG. 11a) and fornix FA (results shown in FIG. 11b) were reduced in all groups except for 2-DG treated rats with fronto-parietal CCI, suggesting that white matter integrity is preserved or repaired in this group compared to saline treated rats or rats with temporo-parietal CCI.

ANOVA uncovered a significant (p=0.038) interaction of CCI location by treatment for CC FA, where FA was highest for fronto-parietal, 2DG treated rats. This substantiated the in vivo findings of increased FA in 2DG treated rats consistent with preserved or repaired white matter compared to saline treated rats (see FIGS. 11a and 11b).

Ex vivo DTI found TBI location by treatment interactions in both the CC and in the fornix, where reduced FA was found for both treatment groups in the temporo-parietal CCI group, but only the saline treated animals showed reduced FA in the fronto-parietal CCI group.

EXAMPLE 2

TBI Clinical Trial Protocol

Previous attempts to develop effective treatment for TBI have included a variety of interventions seeking to reduce primary injury severity and secondary injury cascades contributing to progression after the initial injury. While there is extensive evidence in the experimental literature that many drugs and therapeutic interventions have neuroprotective effects against TBI in animal models, to date no therapies with demonstrated neuroprotective properties against experimental TBI have shown efficacy in human clinical trials (see Loane & Faden, 2010, "Neuroprotection for traumatic brain injury: translational challenges and emerging therapeutic strategies," TIPS 31(12): 596). Among the potential explanations for the failure to demonstrate effects of neuroprotective compounds in human clinical trials is the complexity and variability of human TBI and limitations in clinical trial design that reduce sensitivity of detecting meaningful therapeutic structural and functional effects. The wide range of location and lesion severity in human TBI including damage with great heterogeneity results in variability of direct measurements of the extent of damage, which in turn limits sensitivity for detecting treatment effects with statistical reliability across treatment groups. The invention as described herein permits the skilled artisan to design robust clinical trials to establish in humans the effectiveness of 2DG in the treatment of TBI and to monitor its therapeutic effects against structural brain damage in humans with TBI.

In the embodiments described in Example 1, 2DG notably reduced progression of damage and alterations occurring between one week and six months following initial injury; however, these experiments did not address whether treatment reduced the severity of the initial injury. Example 1 demonstrated that a limited 2DG treatment period favorably modified cellular processes around the time of initial injury with outcomes that only manifested later in the time course of the progressive structural alterations induced by TBI. For those skilled in the art of clinical trial design, Example 1 teaches that neuroprotective effects of TBI resulting from 2DG treatment for a limited period of time will be observed as a reduced rate of progression of structural damage in serial imaging studies in an individual experiencing TBI. The invention thus teaches that the neuroprotective effects of 2DG against TBI will be detected as differences in the extent of disease progression as well as potentially in the rate of progression of initial injury in treated individuals compared to untreated controls. Further, Example 1 teaches that these effects can be detected by serial imaging studies such as computerized tomography (CT), magnetic resonance imaging (MRI), and diffusion tensor imaging (DTI) that can be readily applied by those skilled in the art.

As an example of such a clinical trial, individuals with acute TBI who are receiving conventional medical and surgical care as needed further undergo imaging studies consisting of an initial CT, MRI, or DTI scan characterizing the location, extent, and features of the injury. Information obtained from these scans include regions of interest (ROIs) corresponding to specific lesions and the outlines of the lateral ventricles as described in preceding sections. Such patients are then randomized to acute treatment with either 2DG (in dosages of, for example, 50 mg/kg daily for 2 weeks) or an equivalent volume of saline. The CT, MRI, or DTI scans are repeated at 1 week, 1 month, and 6 months with measurement of ROIs defining the extent of lesions and ventricle volumes. The rate of progression of ROIs from initial to subsequent interval measurements are then compared in 2DG vs. saline treated groups. The initial measurement of ROIs in each individual is unique to that individual and serves as a "within subject" control, enabling precise in vivo measurement of progression of structural abnormalities including ventricular volume, MD, and regional FA as described above and also permits comparison of treatment effects across relevant ranges of injury severity represented in the study population. This clinical trial design as informed and guided by the methods disclosed herein using initial measurements as a within subject control for structural injury progression thus reduces variability due to between-subject differences that have confounded prior studies with other ameliorative agents. In addition, such studies advantageously have reduced sensitivity to detecting treatment effects in a complicated and heterogeneous population with TBI. The clinical trial design informed by the methods disclosed herein can directly determine the extent to which 2DG treatment reduces structural progression of TBI and its accompanying adverse consequences.

All patents, patent applications, scientific article and other sources and references cited herein are explicitly incorporated by reference herein for the full extent of their teachings as if set forth in their entirety explicitly in this application.

It should be understood that the foregoing disclosure emphasizes certain specific embodiments of the invention and that all modifications or alternatives equivalent thereto are within the spirit and scope of the invention as set forth in the appended claims.

What we claim is:

1. A method for reducing severity, progression and associated symptoms of a traumatic brain injury comprising administering to an animal in need thereof a therapeutic amount of an antiglycolytic compound, wherein the severity, progression and associated symptoms of the traumatic brain injury is selected from the group consisting of concussion, progressive brain atrophy, brain cell loss, brain tissue structure reorientation due to injury, and white matter damage.

2. The method of claim 1, wherein the antiglycolytic compound is 2-deoxyglucose (2-DG), 3-deoxy-D-glucose, 4-deoxy-D-glucose, 5-deoxy-D-glucose, 2, n-deoxy-D-glucose, where n=3-5, n, m deoxy-D-glucose, where n=2-5 and m=integers from 2-5 excluding n, sugars that can be metabolized into 2-DG, halogenated and other conjugated derivatives of deoxy sugars, conjugated deoxy sugars that are metabolized to 2-DG, and antiglycolytic compounds having antiglycolytic effects similar to 2-DG.

3. The method of claim 2, wherein the antiglycolytic compound is 2-DG.

4. The method of claim 1, wherein the animal is a human.

5. The method of claim 1, wherein the antiglycolytic compound is administered to the animal for two weeks.

6. The method of claim 1, wherein the antiglycolytic compound is administered to the animal for over two weeks.

7. A method for reducing severity and progression of concussion resulting from a traumatic brain injury comprising administering to an animal in need thereof a therapeutic amount of 2-deoxyglucose.

\* \* \* \* \*